United States Patent
Chandran et al.

(10) Patent No.: US 6,599,999 B1
(45) Date of Patent: *Jul. 29, 2003

(54) HAIR CARE COMPOSITIONS CONTAINING POLYMERIC N-VINYL ACETAMIDE AND METHODS OF TREATING HAIR

(75) Inventors: Rama S. Chandran, Bridgewater, NJ (US); Jean-Pierre Leblanc, Somerville, NJ (US); Hideaki Hanazawa, Osaka (JP)

(73) Assignee: National Starch and Chemical Investment Holding Corporation, New Castle, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/314,389

(22) Filed: May 19, 1999

Related U.S. Application Data

(63) Continuation of application No. 08/837,233, filed on Apr. 10, 1997, now abandoned, which is a continuation-in-part of application No. 08/794,959, filed on Feb. 4, 1997, now abandoned.

(51) Int. Cl.[7] ..................... C08F 120/54; C08F 120/56; A61K 7/06; A61K 7/11
(52) U.S. Cl. ................. 526/303.1; 526/307.1; 526/307.3; 424/70.11; 424/70.16; 424/70.31; 424/70.13
(58) Field of Search ............... 424/70.17, 70.11, 424/70.31, 70.13, 70.16; 526/307, 307.4, 303.1, 307.1, 307.3

(56) References Cited

U.S. PATENT DOCUMENTS

| | | | |
|---|---|---|---|
| 2,628,224 A | 1/1953 | Le Sueur | |
| | | Cairns et al. ............. 260/89.7 | |
| 3,212,972 A | 10/1965 | Bailey, Jr. ................. 167/87.1 |
| 3,285,819 A | 11/1966 | Blance et al. ............... 167/87.1 |
| 4,240,450 A | 12/1980 | Grollier et al. ................. 132/7 |
| 4,402,977 A | 9/1983 | Grollier et al. ............... 424/70 |
| 4,421,602 A | 12/1983 | Brunnmueller et al. .. 162/168.2 |
| 4,578,515 A | 3/1986 | Dawson et al. ............. 564/215 |
| 4,623,699 A | 11/1986 | Brunnmueller et al. ..... 525/355 |
| 4,713,236 A | 12/1987 | Hoover et al. ................. 424/70 |
| 4,906,777 A | 3/1990 | Pinschmidt, Jr. et al. ... 564/215 |
| 4,942,259 A | 7/1990 | Parris et al. ................. 564/187 |
| 5,037,927 A | 8/1991 | Itagaki et al. ............ 526/307.7 |
| 5,037,930 A | 8/1991 | Shih .......................... 527/301 |
| 5,064,909 A | 11/1991 | Itagaki et al. ............... 525/340 |
| 5,155,167 A * | 10/1992 | Pinschmidt et al. .......... 525/60 |
| 5,262,008 A | 11/1993 | Moench et al. .......... 162/168.2 |
| 5,270,379 A | 12/1993 | McAndrew et al. ........ 524/555 |
| RE34,713 E | 8/1994 | Itagaki et al. ............ 525/328.4 |
| 5,373,076 A | 12/1994 | Pinschmide et al. ..... 526/303.1 |
| 5,455,042 A * | 10/1995 | Sakai et al. .................. 424/443 |
| 5,478,553 A | 12/1995 | Chandran et al. ........ 424/40.17 |
| 5,609,857 A * | 3/1997 | Chandran et al. ......... 424/70.17 |
| 5,632,977 A * | 5/1997 | Chandran et al. ........ 424/70.17 |
| 5,849,280 A * | 12/1998 | Rechelbacher et al. .. 424/70.11 |
| 6,090,375 A * | 7/2000 | Rechelbacher et al. .. 424/70.11 |

FOREIGN PATENT DOCUMENTS

| | | | |
|---|---|---|---|
| CA | 2040601 | 4/1991 | |
| DE | 873891 | 7/1949 | |
| JP | 5 097 931 | 4/1993 | ........... C08F/26/02 |
| JP | 05271517 | * 10/1993 | |
| JP | 06 127 725 | 5/1994 | ........... C08F/26/02 |
| JP | 06 179 644 | 6/1994 | ......... C07C/233/18 |

* cited by examiner

*Primary Examiner*—Tatyana Zalukaeva
(74) *Attorney, Agent, or Firm*—Karen G. Kaiser

(57) ABSTRACT

The present invention relates to hair care compositions which contain a polymer which is prepared from N-vinyl acetamide (NVAM) monomer and the use of those hair care compositions to treat hair. The polymer may be a homopolymer of NVAM or an interpolymer of NVAM and at least one vinyl monomer. The polymer is present in amounts effective to provide the hair care compositions with hair fixative properties and/or hair conditioning properties.

23 Claims, No Drawings

HAIR CARE COMPOSITIONS CONTAINING POLYMERIC N-VINYL ACETAMIDE AND METHODS OF TREATING HAIR

This application is a continuation of application Ser. No. 08/837,233 filed Apr. 10, 1997 now abandoned which in turn is a continuation-in-part of application Ser. No. 08/794,959 filed Feb. 4, 1997 and now abandoned.

FIELD OF THE INVENTION

This invention relates to hair care compositions which comprise a polymer prepared from N-vinyl acetamide monomer.

BACKGROUND OF THE INVENTION

In their most basic form, hair care compositions contain a film-forming resin, typically a polymer. The resin can be applied to the hair in the form of a spray, a gel, a mousse, a rinse, a lotion, a conditioner or a shampoo.

In aerosol hair spray systems, the resin usually is dissolved in an organic solvent, such as ethanol or isopropyl alcohol, and delivered via a propellant, which is usually a volatile hydrocarbon. These systems are becoming less desirable due to the consumers' perception that alcohol in hair sprays can dry and damage hair, and due to environmental regulations limiting the emission of volatile organic compounds (VOC) into the atmosphere. As used herein, a volatile organic compound is an organic compound containing from 1 to 10 carbon atoms, and which has a vapor pressure of at least 0.1 mm Hg at 20° C. There is an on-going effort by the hair care industry to replace VOC with water. However, the inclusion of significant amounts of water in hair fixative compositions has created problems relating to solubility and dispersability of the hair fixative resin in the compositions, to application of the hair fixatives to the hair and to performance of the hair fixative once applied to the hair.

There is a need in the industry for low VOC, aqueous-based, hair fixative compositions and hair fixative polymers which are dispersible or soluble in water, which can be applied readily to the hair, and which provide acceptable hair fixative properties, such as strength, i.e., holding power or stiffness, humidity resistance, film clarity, aesthetics and removability from hair using conventional shampoo and/or water.

One such approach to lower VOC hair fixatives is disclosed in U.S. Pat. No. 5,021,238, in the name of Martino et al. Two-phase, aqueous-based, hair-fixing aerosol systems which utilize dimethyl ether as a propellant are disclosed. The system can be shaken to form a semi-stable emulsion or mixture which is stable for a time sufficient for spraying.

Another approach to significantly reducing or totally eliminating VOC in hair fixatives is the use of water-dispersible or water-soluble polymers in an aqueous-based hair fixative gel. Such gels which are available currently utilize poly(vinyl pyrrolidone) (PVP) or derivatives thereof, such as poly(vinyl pyrrolidone/vinyl acetate) copolymers (PVPNA), as the hair fixative resin contained therein. PVP is very sensitive to water or humidity, which deteriorates the fixative properties. It is desirable, then, to find a water-soluble polymer to replace PVP. The polymer should be less sensitive to water, form clear films upon drying, and provide the hair fixative gels with hair fixative properties which are as good as or better than hair fixative gels which contain PVP as the fixative resin. It recently has been reported that polymers prepared from N-vinyl formamide may be utilized in hair fixative compositions, including gels, mousses, sprays, etc.

Hair conditioning agents are functional additives used in hair care products such as lotions, shampoos, creme rinses, mousses and setting gels to improve the tactile and physical properties of hair. Cationic quaternary ammonium compounds, both mono- and di-functional, low molecular weight quaternary ammonium salts and certain high molecular weight polymers, are employed as conditioning additives in hair care products such as shampoos, conditioners, creme rinses, mousses, sprays and setting gels to impart wet and dry combability, improve feel, enhance curl retention and impart antistatic properties to hair. The Cosmetics, Toiletries and Fragrances Association (INCI) has established a designation index for compounds employed in cosmetic and toiletry products. Two low molecular weight quaternary ammonium compounds that are commonly used in hair care products because of their low cost are stearylbenzyldimethylammonium chloride (INCI designation—stearalkonium chloride) and cetyltrimethylammonium chloride (INCI designation—cetrimonium chloride).

The high molecular weight, cationic quaternary ammonium polymers (polyquats) are being used increasingly in hair care products because of their reported advantages over the simple quaternary ammonium salts in enhancing wet combability, mending split ends and improving appearance. Commonly used polyquats include: Celquat® (INCI designation—Polyquaternium 10) from National Starch and Chemical Company, a quaternized cellulose; Gafquat® (INCI designation—Polyquaternium 11) from International Specialty Products, a quaternized copolymer of vinylpyrrolidone and dimethylaminoethyl methacrylate; and Merquat® 550 (Polyquaternium 7) from Calgon, a homopolymer of dimethyldiallylammonium chloride.

These quaternary ammonium conditioning additives have in common the quaternary ammonium functional group:

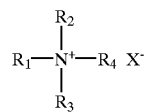

where $R_1$ through $R_4$ may be various substituted or unsubstituted alkyl or aryl substituents, or in the case of the polyquats, represent alkylene or arylene segments of a polymer chain. Associated with the positively charged quaternary ammonium nitrogen atom is a negatively charged counterion. This anion, $X^-$ may be a halide, hydroxide, methylsulfate or similar negatively charged group.

While it is known that certain copolymers prepared from vinyl pyrrolidone or N-vinyl formamide may be used as hair conditioning additives in hair conditioning compositions and as hair fixative resins in hair fixatives, it is desirable to develop new polymers which can be used in such hair care compositions.

SUMMARY OF THE INVENTION

The present invention relates to hair care compositions which comprise an essentially non-crosslinked polymer which is prepared from N-vinyl acetamide monomer (NVAM). The polymer may be a homopolymer prepared from NVAM or an interpolymer prepared from NVAM and a vinyl monomer other than the NVAM. The hair care composition also includes an ingredient selected from the group consisting of a conditioning agent, an emulsifier, a surfactant, a rheology modifier, a gelling agent, an opacifier, a stabilizer, a preservative, a sequestering agent, a chelating agent, a pearling agent, a clarifying agent, a fragrance, a colorant, a propellant, water and an organic solvent. The polymer is present in amounts effective to provide the inventive hair care composition with hair fixative properties and/or with hair conditioning properties. The invention also relates to methods of treating hair which comprise applying to the hair the hair care compositions of the present invention and, optionally, removing excess hair care composition from the hair.

DETAILED DESCRIPTION OF THE INVENTION

NVAM polymerizes to form a nonionic, water-soluble polymer which forms clear, non-tacky films upon drying. The present invention is directed to hair care compositions which utilize water-soluble polymers which are prepared from NVAM. NVAM is available from Showa Denko K.K., Tokyo, Japan. Processes for making NVAM are known to those skilled in the art and are reported in Japanese publications JP 08 81428 and JP 08 134029.

The polymer may be a homopolymer of NVAM or may be an interpolymer prepared from NVAM and at least one vinyl monomer(s) other than the NVAM. Preferably, the interpolymer will be prepared from at least about 10 weight percent of NVAM, with the balance of the vinyl monomer (s). The term "vinyl monomer", as used herein, refers to vinyl monomers which are copolymerizable with the NVAM and expressly excludes the NVAM. Suitable vinyl monomers include, (a) styrene and derivatives thereof, such as alkyl-substituted styrene, (b) $C_1$–$C_{18}$ alkyl esters of acrylic acid, (c) $C_1$–$C_{18}$ alkyl esters of methacrylic acid, (d) vinyl esters of the formula $CH_2$=CH—OCOR where R is $C_1$–$C_{18}$, (e) alkyl substituted acrylamides and methacrylamides of the formula $CH_2$=CR—$CONR_1R_2$ where R is H or $CH_3$; $R_1$ is H or $C_1$–$C_{12}$ and $R_2$ is $C_1$–$C_{18}$, (f) monoesters and diesters of fumaric, itaconic and maleic acids, (g) vinyl ethers such as methyl vinyl ether, isobutyl vinyl ether and the like, (h) hydroxy-substituted acrylates and methacrylates such as hydroxyethyl acrylate, hydroxypropyl acrylate, hydroxyethyl methacrylate, hydroxypropyl methacrylate and the like, (i) vinyl monomers containing an amine selected from the group consisting of secondary, tertiary and quaternary amines, such as n-vinyl imidazole, t-butylaminoethyl methacrylate (t-BAEM), dimethylaminoethyl methacrylate (DMAEMA), diethylaminoethyl methacrylate (DEAEMA), dimethylaminopropyl methacrylamide (DMAPMA) and the quartemized derivatives thereof such as methacrylatoethyltrimethyl ammonium chloride (MAPTAC), methacrylatoethyltrimethyl ammonium sulfate (MAETAS) and dimethyl diallyl ammonium chloride (DMDAAC), (j) acrylamide, (k) non-alkyl substituted acrylamides such as diacetone acrylamide and (l) cyclic amides such as vinyl pyrrolidone and n-vinyl caprolactam. Preferably, the vinyl comonomer is selected from the group consisting of methyl acrylate, methyl methacrylate, 2-hydroxyethyl acrylate, 2-hydroxyethyl methacrylate, 2-hydroxypropyl acrylate, 2-hydroxypropyl methacrylate, vinyl acetate, oligoethylene glycol monomethacrylate, N-vinyl pyrrolidone and the vinyl monomers containing an amine selected from the group consisting of secondary, tertiary and quaternary amines.

In order to function as a hair fixative, the hair care composition and the hair fixative resin, i.e., poly(vinyl acetamide) (PVAM) polymer, must possess certain hair fixative properties. For instance, the compositions must be capable of forming flexible, clear, low-tack or non-tacky films at room temperature. Once applied to the hair, the films must possess sufficient stiffness and humidity resistance to hold the hair in place under conditions normally encountered by the user thereof, yet must be readily removable from the hair by conventional shampoos and/or water. Therefore, the polymers prepared according to the present invention are essentially non-crosslinked, as crosslinking of the polymer tends to reduce water solubility and therefore water removability. Accordingly, the polymers are not prepared utilizing crosslinking agents comprising polymerizable compounds having at least two unsaturated groups in one molecule at any levels which would result in significantly reduced water removability properties of the polymers. Preferably, the polymers are prepared with less than 0.5 weight percent of such compounds, based on total weight of monomer used to prepare the polymer, more preferably less than 0.2 weight percent, and even more preferably, less than 0.1 weight percent of such compounds. Most preferably, the polymers are prepared in the absence of such crosslinking compounds. Such agents include, without limitation, N,N'-lower alkylene bisacrylamides, alkylene glycol di(meth)acrylates, polyalkylene glycol di(meth)acrylates, divinyl compounds, and compounds such as those disclosed in U.S. Pat. No. 5,280,095, Aizawa et al., the content of which is hereby incorporated by reference as if set forth in its entirety. The polymer preferably will have a glass transition temperature (Tg) which is effective to form clear, low tack or non-tacky films at room temperature. If the Tg is too low, the films formed may be too tacky and may not possess adequate stiffness and humidity resistance.

Gel fixatives according to the present invention comprise as a hair fixative resin a homopolymer which is prepared from NVAM, or interpolymers prepared from NVAM and at least one vinyl monomer(s). Unlike gels prepared using poly(vinyl pyrrolidone) (PVP), a well known conventional hair fixative resin, and gels prepared using poly(vinyl formamide) (PVF), a recently reported hair fixative resin, gels prepared using PVAM as the fixative resin provide exceptional and superior clarity and color to both water and ethanol-based gel formulations. When compared to gel fixatives prepared with PVP and PVF, gels prepared with PVAM unexpectedly exhibited comparable humidity resistance. When compared to gels prepared with PVF, the aging profile of the PVAM homopolymer-based gel was better than that of a PVF-based or PVP-based gel. Also, PVAM offers more formulation flexibility than PVF due to its dual water and ethanol solubility.

While organic hydrocarbon solvents such as ethanol may be used in preparing hair fixative gels according to the present invention, the gel fixatives preferably are substantially free of organic hydrocarbon solvents and natural or synthetic oils, such as glycerol esters of higher even-numbered fatty acids, glycerides of palmitic stearic and oleic acid, liquid fatty acid esters, liquid fatty alcohols, paraffin oils, esters of polyhydric alcohols and polyethylene alcohols.

The hair fixative gels of the invention comprise an amount of the hair fixative polymer which is effective to impart hair fixative properties to the gels. Where the level of polymer is too high, the gels and films formed therefrom exhibit unacceptable haziness. Where the level of polymer is too low, properties such as stiffness and humidity resistance are adversely affected. Typically, the gels comprise from about 0.05 to about 15 weight percent of the polymer, preferably from about 0.1 to about 10 weight percent, and more preferably from about 2 to about 7 weight percent of the polymer, based on the total weight of the gel. The hair fixative gels also comprise a rheology modifier, e.g., a gelling agent, in amounts effective to form a gel. Preferably, the gels comprise from about 0.05 to about 3 weight percent of the gelling agent, more preferably from about 0.1 to about 1.0 weight percent of the gelling agent, based on the total weight of the hair fixative gel. Examples of such gelling agents include synthetic polymers such as the acrylic-based Carbopol® series of thickeners available from B.F. Goodrich, Cleveland, Ohio and associative thickeners such as Aculyn, available from Rohm & Haas, Philadelphia, Pa. Other exemplary gelling agents include, cellulosic thickeners, such as derivatized hydroxyethyl cellulose and methyl cellulose, starch-based thickeners, such as acetylated starch, and naturally occurring gums, such as agar, algin, gum arabic, guar gum and xanthan gum.

In certain embodiments, the rheology will be such that the gels may be applied via a spray pump. That is to say, the gels will be shear thinning to the extent that they may be applied via a spray pump and retain their hair fixative properties once applied to the hair. As one skilled in the art will appreciate, the particular Theological properties required for a spray pump application may be dependent upon factors such as the spray nozzle utilized, gel composition, the organic solvent system utilized, if any, and the like. One skilled in the art, having the benefit of the teachings of the present invention, will be able to ascertain the particular rheological properties required for a particular spray pump application.

In other embodiments, the hair fixative compositions may be in the form of an aerosol or non-aerosol spray, a mousse or a hair-setting lotion. The compositions may be aqueous, i.e. they are substantially free of organic solvents, or non-aqueous, although aqueous hair fixative compositions are preferred. The compositions may contain up to 40 weight percent, preferably up to 35 weight percent, of propellants, such as ethers, compressed gases, halogenated hydrocarbons and hydrocarbons. Exemplary propellants are dimethyl ether, propane, butane and 1,1-difluoroethane. Non-aqueous hair fixative compositions may further include solvents such as ethanol, isopropanol, acetone, dimethoxymethane and methyl ethyl ketone. The compositions may further include other materials or additives such as fragrances, preservatives, colorants, plasticizers, emulsifiers, conditioners, neutralizers, glossifiers and the like. Such propellants, solvents and materials or additives are commonly used in hair fixative compositions known heretofore.

Mousses according to the present invention comprise an amount of the polymer which is effective to impart hair fixative properties to the mousse, similar to gel fixatives. The mousses further comprise from about 0.25 to 6 weight percent, preferably 0.25 to 3 weight percent, of an emulsifier. The emulsifier may be nonionic, cationic, anionic or amphoteric. Exemplary nonionic emulsifiers include Tergitol® NP 15 (INCI designation—Nonoxynol 15) and Brij 97 (INCI designation—Oleth 10). The mousses also comprise from about 2.5 to 25 weight percent, preferably 5 to 15 weight percent, of a propellant as discussed above. The mousses may comprise additional ingredients as discussed above, with the balance of the mousse comprising water.

In order to function as a hair conditioner, the hair care composition must possess certain hair conditioning properties. Such properties include, for example, substantivity of the conditioning agent on the hair without excessive build-up and enhancement of hair manageability, i.e., wet combability, dry combability, neutralization of static charge generated by combing and ease of styling. Other properties include lubrication of the hair to reduce friction between hair and comb and to minimize tangling. The additive should also soften the hair and impart gloss to dull hair and smooth the feel of the hair by filling in gaps or flattening cuticle scales. It is also advantageous for the hair conditioner to improve set retention of the hair.

In order to provide the hair care compositions with hair conditioning properties, the inventive polymers comprise the polymerized residue of the vinyl monomer containing at least one amine group selected from the group consisting of secondary, tertiary and quaternary amines, in amounts effective to provide the hair care compositions with hair conditioning properties. Particularly preferred vinyl monomers which contain the amine group are the quaternary amine-containing monomers. Suitable monomers containing a quaternary amine include, for example, methacrylatoethyltrimethyl ammonium sulfate (MAETAS), methacrylamidopropyltrimethyl ammonium chloride (MAPTAC) and dimethyl diallyl ammonium chloride (DMDAAC). Preferred quaternary amine-containing moieties are MAPTAC and DMDAAC.

The secondary and tertiary amines may be nonionic or cationic, although cationic amines are preferred. In certain embodiments, nonionic secondary and tertiary amines, such as t-butyl aminoethyl methacrylate (t-BAEM), dimethylaminoethyl methacrylate (DMAEMA) and dimethylaminopropyl methacrylamide (DMAPMA) are converted to cationic amines. One method for such conversion is to neutralize the secondary or tertiary amines with an appropriate acid to form an ammonium salt. Alternatively, the secondary or tertiary amines may be reacted with quaternizing agents to form quaternary amines. Such quaternizing agents include, for example, alkyl halides such as methyl chloride, or dialkyl sulfates such as dimethyl sulfate. One skilled in the art will recognize that there may be other routes to convert the nonionic secondary and tertiary amines to cationic amines. Suitable monomers containing a nonionic tertiary amine include, for example, DMAEMA and DMAPMA. Suitable monomers containing a nonionic secondary amine include, for example, t-BAEM.

In embodiments exhibiting hair conditioning properties, the polymer may prepared from NVAM and the vinyl amine-containing monomer. Preferably, the copolymer is prepared with from about 50 to about 99 weight percent of NVAM and from about 1 to about 50 weight percent of the vinyl amine-containing monomer. More preferably, the copolymer is prepared with from about 60 to about 90 weight percent of NVAM and from about 30 to about 10 weight percent of the vinyl amine-containing monomer. Most preferably, the copolymer is prepared with from about 75 to about 90 weight percent NVAM and from about 25 to about 10 weight percent of the vinyl polymerizable moiety.

The hair conditioning compositions of the present invention comprise an amount of the hair conditioning polymer which is effective to impart hair conditioning properties to the hair conditioning compositions. Typically, the hair conditioning compositions comprise from about 0.1 to about 15 weight percent of the polymer, preferably from about 0.25 to about 10 weight percent of the polymer, based on the total weight of the hair conditioning composition.

In one embodiment, the hair conditioning composition is a conditioning lotion. In addition to the inventive conditioning polymer, the lotion may further comprise other conditioning agents, such as cationic surfactants, fatty acid salts, hydrolyzed proteins such as collagen, keratin and amino acids, and oily materials such as lanolin, fatty alcohols, waxes and botanical oils. The lotion may also further comprise other ingredients such as emulsifiers, rheology modifiers, opacifiers, pearlizers, stabilizers, preservatives, fragrances and colorants. In certain embodiments, the lotion may be applied via a spray delivery system.

In other embodiments, the hair conditioning composition is a conditioning shampoo. The shampoos generally comprise primary surfactants for cleansing and foam, secondary surfactants for cleansing, foam boosting and conditioning and additional additives for special performance, stability, fragrance and color. More specifically, these aqueous-based systems may contain surfactants, conditioning agents such as cationic or amphoteric surfactants, oily materials, proteins, botanicals, synthetic resins and silicone polymers, in addition to other additives such as sequestering or chelating agents, viscosity modifiers, opacifying, pealing or clarifying agents, stabilizers, fragrances, colorants and preservatives.

The hair conditioning composition also may comprise a gelling agent in amounts effective to form a conditioning gel. Preferably, the conditioning gel comprises from about 0.05 to about 3 weight percent of the gelling agent, more preferably from about 0.1 to about 1.0 weight percent of the gelling agent, based on the total weight of the conditioning gel. Examples of such gelling agents include synthetic polymers such as the acrylic-based Carbopol® series of thickeners available from B.F. Goodrich, Cleveland, Ohio and associative thickeners such as Aculyn®, available from Rohm & Haas, Philadelphia, Pa. Additionally, crosslinked, N-vinyl carboxylic acid amide microgels such as those reported in U.S. Pat. No. 5,280,095 may be used in combination with the polymers of the present invention in order to prepare gels for use in hair care. These microgels are distinct from the polymers of the present invention in that they are prepared in amounts of a polymerizable compound having at least two unsaturated groups in one molecule which are effective to produce microgels having a thixotropic property as a thickener. Other exemplary gelling agents include, cellulosic thickeners, such as derivatized hydroxyethyl cellulose and methyl cellulose, starch-based thickeners, such as acetylated starch, and naturally occurring gums, such as agar, algin, gum arabic, guar gum and xanthan gum.

In yet other embodiments, the hair conditioning composition may be in the form of mousse or spray. The mousse or spray may contain, in addition to the ingredients mentioned herein above, up to 40 weight percent, preferably up to 35 weight percent, of propellants such as ethers, compressed gases, halogenated hydrocarbons and hydrocarbons. Exemplary propellants are dimethyl ether, propane, butane, 1,1-difluoroethane, and mixtures thereof. The mousses further comprise from about 0.25 to 6 weight percent, preferably 0.25 to 3 weight percent, of an emulsifier. The emulsifier may be nonionic, cationic, anionic or amphoteric. Exemplary nonionic emulsifiers include Tergitol® NP 15 (INCI designation—Nonoxynol 15) and Brig® 97 (INCI designation—Oleth 10). The mousses also comprise from about 2.5 to 25 weight percent, preferably 5 to 15 weight percent, of a propellant as discussed above. The mousses may comprise additional ingredients as discussed above, with the balance of the mousse comprising water.

The hair conditioning compositions may include organic solvents to modify certain properties of the hair conditioning compositions, such as viscosity, solubility or drying. Typical solvents include, for example, ethanol, isopropanol, acetone, dimethoxymethane and methyl ethyl ketone. When used, the amounts of organic solvents preferably are less than about 40 weight percent, more preferably less than about 30 weight percent and even more preferably are minimized. Most preferably, the compositions will be free of organic solvents.

The hair care compositions will contain from about 0.1 to about 20 weight percent of an ingredient selected from the group consisting of conditioning agents, emulsifiers, surfactants viscosity modifiers, gelling agents, opacifiers, stabilizers, preservatives, sequestering agents, chelating agents, pearling agents, clarifying agents, fragrances and colorants. Preferably, the composition will comprise from about 1 to about 10 weight percent of the one or more ingredients.

The invention is also directed to methods of treating hair which comprise applying to the hair an the hair care composition which comprises the polymer of the present invention in amounts effective to provide the hair care composition with a property selected from the group consisting of a hair fixative property and a hair conditioning property, as those properties are discussed herein, and an ingredient selected from the group consisting of conditioning agents, emulsifiers, surfactants viscosity modifiers, gelling agents, opacifiers, stabilizers, preservatives, sequestering agents, chelating agents, pearling agents, clarifying agents, fragrances, colorants, and propellants. Excess hair care composition may be removed from the hair, for instance in the case of a conditioning shampoo or rinse. In other embodiments, such as gels, mousses and hair sprays, the hair care composition generally is not removed until the hair is washed later with water or shampoo.

The following examples are indicative of preferred hair care compositions and hair care polymers utilized therein. They are not intended and should not be construed to limit the scope of the claims appended hereto. All percentages noted herein are weight percent unless noted otherwise.

POLYMER PREPARATION

Preparation of PVAM Homopolymer by Precipitation Polymerization

In a 2-l flask equipped with a condenser were introduced 22.5 g of NVAM, 250 g of ethyl acetate, and, over a 5 minute period, 0.9 mmol of t-amyl peroxypivalate. Two slow-adds are added 10 minutes later: the first one consisting of 177.5 g of NVAM and 458.5 g of ethyl acetate and the second one consisting of 5.4 mmol of t-amyl peroxypivalate and 63.5 g of ethyl acetate. The slow-adds are added over periods of 3 and 6 hours, respectively, while maintaining reflux in the reaction system. The reaction is continue for one more hour before filtration of the mixture. The powder polymer is dried for solvent removal in a heated oven.

Preparation of PVF Homopolymer by Precipitation Polymerization

Into a 2-l flask equipped with a stirring shaft powered by a mechanical stirrer, a heating bath, a thermometer and a reflux condenser were added as an initial charge 22.5 g of NVF, 250 g of 1-propanol, and 0.2 g of t-butyl peroctoate. The mixture was purged with nitrogen and heated to reflux. At this point the two following slow-adds were added: nitrogen-purged mixture of 177.5 g of NVF and 458.5 g of 1-propanol over a period of 3.5 hours; mixture of 1.0 g of t-butyl peroctoate and 26.5 g of 1-propanol over a period of 4 hours. Reflux was maintained at all times. One hour after the end of the addition of the initiator slow-add, a scavenger initiator slow-add composed of 0.2 g of t-butyl peroctoate and 37 g of 1-propanol were added over a period of 2 hours. The mixture then was held under reflux for an additional 5 hours. After cooling to 70° C., it was filtered and the white polymer precipitate then was dried at 60° C. in an oven for 2 hours and at 130° C. in an oven overnight.

HAIR CARE COMPOSITION PREPARATION

All values reported are parts by weight, based on the total weight of the composition.

Gel composition

| | Ingredient | Parts by Weight |
|---|---|---|
| Part A | polymer | 3.00 |
| | triethanolamine (TEA) | 0.60 |
| | deionized water | 47.85 |
| Part B | Carbopol ® 940 | 0.6 |
| | Dowicil ® 200 (preservative) | 0.10 |
| | deionized water | 47.85 |
| | | 100 |

The polymer and TEA were mixed in D.I. water until homogenous. In a separate vessel, the Dowicil® 200 preservative and Carbopol® 940 thickener were combined with D.I. water and mixed until the Carbopol® went into solution. Dowicil® 200 is available from The Dow Chemical Company, Midland, Mich. Parts A and B were then combined and mixed gently until a clear viscous gel was formed.

Mousse formulation

| Ingredient | Parts by Weight |
|---|---|
| polymer | 2.50 (dry weight) |
| Tergitol ® NP15 surfactant | 0.50[1] |
| Brij ® 97 surfactant | 0.30 |
| Dowicil ® 200 preservative | 0.10 |
| Propellant (20:80/Propane butane) | 10.00 |
| Water | 86.60 |
| | 100.00 |

Procedure: The polymer is dissolved in water with adequate agitation. The surfactants and preservative are added and the solution is mixed until homogenous. The product is filtered and filled into a container. The container is then charged with the propellant. Tergitol® NP15 surfactant is available from Union Carbide Chemical and Plastics Company, Danbury, Conn. Brij® 97 surfactant is available from ICI Specialty Chemicals, Wilmington, Del.

Conditioning Lotion:

| Ingredient | Parts by weight |
|---|---|
| Polymer | 1.00 |
| Carbopol ® 940 thickener | 0.15 |
| Triethanolamine | 0.15 |
| Deionized Water | 98.70 |
| | 100.00 |

Procedure: The Carbopol® 940 thickener is dispersed in water with good agitation. The conditioning polymer is added to the water and mixed until dissolved. While mixing, triethanolamine is added. Mixing is continued until a homogeneous mixture is produced.

Conditioning Shampoo

| Ingredient | Parts by weight |
|---|---|
| polymer | 1.80 |
| TEA Lauryl Sulfate | 25.00 |
| Cocamide DEA | 5.00 |
| Dowicil ® 200 preservative | 0.10 |
| Deionized Water | 68.10 |
| | 100.00 |

Procedure: The conditioning polymer is dissolved in 20 parts water. In a separate container, the remaining water is heated to 70° C. TEA Lauryl Sulfate and Cocamide DEA are then added to the heated water. The polymer solution from step 1 is added to the heated water. The mixture is cooled to 40° C. and the preservative is added. The mixture is cooled to room temperature. Dowicil® 200 is available from The Dow Chemical Company, Midland, Mich.

Conditioning Gel

| | Ingredient | Parts by Weight |
|---|---|---|
| Part A | Polymer | 3.00 |
| | Triethanolamine (TEA) | 0.60 |
| | Deionized Water | 47.85 |
| Part B | Carbopol ® 940 thickener | 0.60 |
| | Dowicil ® 200 preservative | 0.10 |
| | Deionized Water | 47.85 |
| | | 100.00 |

The polymer and TEA are mixed in D.I. water until homogenous. In a separate vessel, the Dowicil® 200 preservative and Carbopol® 940 thickener are combined with D.I. water and mixed until the thickener goes into solution. Parts A and B are then combined and mixed gently until a clear viscous gel is formed.

Conditioning Mousse

| Ingredient | Parts by Weight |
|---|---|
| Polymer | 2.50 |
| Tergitol ® NP15 surfactant | 0.50 |
| Brij ® 97 surfactant | 0.30 |
| Dowicil ® 200 preservative | 0.10 |
| Propellant (20:80/Propane:butane) | 10.00 |
| Water | 86.60 |
| | 100.00 |

Procedure: The conditioning polymer is dissolved in water with adequate agitation. The surfactants and preservative are added and the solution is mixed until homogenous. The product is filtered and filled into a container. The container is then charged with the propellant. Tergitol® NP15 surfactant is available from Union Carbide Chemical and Plastics Company, Danbury, Conn. Brij® 97 surfactant is available from ICI Specialty Chemicals, Wilmington, Del.

EVALUATION OF HAIR CARE COMPOSITIONS

EXAMPLE 1

The PVF and PVAM polymers prepared above, in addition to commercial polymers based on vinyl pyrrolidone, specifically PVP K-90 and PVP K-30, available from International Specialty Products, were formulated into hair fixative gel compositions according to the following formulation and procedures discussed above.

| polymer | 1.5% |
|---|---|
| Carbopol 940 | 0.5% |
| TEA | 0.5% |
| ethanol | 15% |
| D.I. water | q.s. |
| | 100 wt % |

The gels were observed visually to determine initial appearance with respects to color and clarity. The gels were placed in a constant temperature oven at 50° C. for four weeks, after which time visual observations again were made appearance with respects to color and clarity. Results are presented in Table 1.

TABLE 1

| Polymer | initial appearance | appearance after 4 weeks at 50° C. |
|---|---|---|
| PVP K-90 | colorless, clear | light yellow, slightly translucent |
| PVF | colorless, slightly translucent | slight yellow, translucent |
| PVAM | colorless, clear | slight yellow, clear |

The data indicates that gels which utilize PVP or PVF as the hair fixative resin exhibit more aging than do gels which utilize PVAM as the hair fixative resin. Accordingly, PVAM is an improvement over PVP and PVF with respect to aging.

EXAMPLE 2

Alcohol-free gels were prepared at 3% polymer solids utilizing PVAM, PVF and PVP K-90, respectively. The gels were evaluated for thickener comparability (Carbopol 940), by visually observing the clarity of the resultant gels. Initial clarity ratings were made and then the gels ages for three months at 50° C. Aged clarity ratings then were made. Results are presented in Table 2.

TABLE 2

| Polymer | Initial Clarity Rating | Aged Clarity Rating |
|---|---|---|
| PVAM | 1 | 1 |
| PVF | 1 | 4 |
| PVP | 1.5 | 2 |

With a rating of 1 being clear, 2 being slightly hazy, 3 being hazy, 4 being turbid and 5 being opaque, PVAM initially is equivalent to PVF and superior to PVP with respects to thickener compatibility. PVAM is superior to both PVF and PVP with respects to aging.

EXAMPLE 3

Subjective properties of alcohol-free gels prepared in Example 2 utilizing PVAM and PVP, respectively, were compared. Each of the gels was tested on dampened 10 inch Brown Italian hair swatches. To each swatch was applied 0.5 g of the respective gel. The gel was worked into the swatch and each swatch then was evaluated for wet combability. Each swatch then was dried in an oven at 110° F. for two hours. Additional subjective properties evaluated included gloss, stiffness, dry combability, flakiness and static flyaway. Subjective evaluation criteria is presented below. Results are presented in Table 3.

1. Wet combability—The swatch was gently combed several times and rated for ease of comb-out.
2. Gloss—The swatch was visually rated for gloss and sheen.
3. Subjective Stiffness—The swatch was handled by the panelist and rated for stiffness versus softness according to the resistance felt when attempting to bend the hair swatch.
4. Dry Combability—The swatch was gently combed several times and rated for ease of comb-out.
5. Flakiness—The swatch was visually examined for flaking following combing.
6. Static flyaway—The swatch was vigorously combed and then rated for the extent of static flyaway exhibited.

Data acquired from these methods are qualitative and not quantitative, and therefore subjective. However, panelists who participated in these blind studies have been trained in the analysis of hair swatches for these properties. Additionally, the subjective evaluations are statistically analyzed to identify differences at the 90% confidence level.

TABLE 3

| | Gloss | Stiffness | Wet Comb | Dry Comb | Flake | Anti-Stat |
|---|---|---|---|---|---|---|
| PVAM vs. PVP K-90 (control) | 3/8 (=) | 2/8 (=) | 5/8 (=) | 5/8 (=) | 5/8 (=) | 2/8 (=) |

Key:
+ the experimental is statistically superior to the control (7/8 rated superior)
= the experimental is statistically equivalent to the control (2-6/8 equivalent)
− the experimental is statistically inferior to the control (1/8 rated inferior)

As the data indicates, PVAM is equivalent to PVP with respects to subjective properties of alcohol-free gel compositions.

EXAMPLE 4

A 10% percent solids solution of polymer in water was prepared. Transmittance of the solution was determined by the ratio of light transmitted by the polymer solution to that of the pure water. Measurement was conducted at 400 nm utilizing a spectrophotometer.

TABLE 4

| Polymer | solvent | transmittance |
|---|---|---|
| PVP K-90 | DI water | 87.5% |
| PVF | DI water | 85.2% |
| PVAM | DI water | 90.0% |

As a 2% difference in transmittance is noticeable to the eye, the results indicate that PVAM is superior to both PVP and PVF with respect to clarity in aqueous solutions.

EXAMPLE 5

The PVAM homopolymer prepared above was compared with PVP K-30, PVP K-90 and the PVF homopolymer prepared above for performance differences, particularly in aerosol hair spray applications. Each polymer was tested for hydrocarbon tolerance (Table 5a) and for sprayability (Table 5b) by preparing the anhydrous systems described below and then by observing the systems for appearance in hydrocarbon solvents and for sprayability, in addition to particle size measurement of the aerosol sprays (Table 5b).

TABLE 5a

Hydrocarbon Tolerance (3% polymer solids, anhydrous systems, A-46 propellant)

| Polymer | A-46 Hydrocarbon |
|---|---|
| PVAM | 60% - very slightly hazy |
| PVP K-30 | 60% - very slightly hazy |
| PVP K-90 | 60% - hazy, slight precipitate |

PVAM tolerates about 60% hydrocarbon, similar to PVP K-30. The higher molecular weight PVP K-90 develops precipitate at the 60% hydrocarbon level. All polymers are incompatible with 65% hydrocarbon. Accordingly, PVAM is equivalent to PVP with respect to hydrocarbon compatibility.

TABLE 5b

Aerosol Sprayability (4% polymer solids, anhydrous systems, 25% A-46)

Particle Size Analysis (microns)

| Sample | Mean | Median | Spray Rating (A = best) |
|---|---|---|---|
| PVAM | 92.50 | 86.01 | B+ |
| PVP K-30 | 47.04 | 43.33 | A |
| PVP K-90 | NA | NA | D (unacceptable) |

Molecular weight and viscosity of PVP K-90 are very high and thus that particular polymer generally is unacceptable for use in anhydrous aerosol hair spray applications. However, the lower molecular weight PVP K-30 is usable in anhydrous aerosol compositions and exhibits the best sprayability, while PVAM exhibits good sprayability in anhydrous aerosols.

EXAMPLE 6

Procedures for Subjective Evaluation of Compositions

PVAM was evaluated against PVP controls with respect to the following properties: dry combability, gloss, static flyaway and flakiness. Details of the test are described below.

The polymers were evaluated in 4% active anhydrous aerosol systems. Virgin dark brown hair was obtained from DeMeo Brothers, 129 W. 28th Street, New York, N.Y. 10001. A separate 5.25 gram hair swatch, 10 inches in length, was used for each polymer or water treatment.

The swatches were sprayed two seconds per side from a distance of six inches and allowed to dry at ambient conditions for one hour. The swatch samples were grouped as pairs (PVAM-treated versus PVP-treated). A total of eight pairs of samples were evaluated. Performance was evaluated by a trained panel of two members, who compared the coded, inventive polymers to a control of PVP. Each member on the panel rated four pairs of samples (PVAM vs. PVP) as being inferior/superior (−/+) one to the other, or as no statistical difference (NS). Eight pairs in all were tested for each polymer. Each swatch was evaluated for subjective properties as set forth in Example 3, with the exception that wet combability evaluation was excluded. Results of the evaluation are found in Table 6.

TABLE 6

Subjective Evaluations (4% polymer solids, anhydrous aerosols, 25% A-46)

| Comparison | Gloss | Stiffness | Dry Comb | Flake | Anti-Stat |
|---|---|---|---|---|---|
| PVAM vs. PVP K-90 (control) | 4/8 (=) | 0/8 (−) | 8/8 (+) | 8/8 (+) | 3/8 (=) |
| PVAM vs. PVP K-30 (control) | 3/8 (=) | 6/8 (=) | 6/8 (=) | 1/8 (−) | 7/8 (+) |

Key:
+ the experimental is statistically superior to the control (7/8 rated superior)
= the experimental is statistically equivalent to the control (2-6/8 equivalent)
− the experimental is statistically inferior to the control (7/8 rated inferior)

As expected, PVP K-90 is stiffer than the PVAM polymer, while the PVAM polymer is superior with respect to dry combability and flakiness. The two resins are equivalent with respect to gloss and anti-static. The PVAM polymer is directionally superior in stiffness to PVPK-30 is superior with respect to anti-static is inferior with respect to flakiness and is equivalent as to gloss, stiffness and dry combability. One conclusion to draw from the data is that polymers prepared from PVAM generally are comparable with respect to subjective evaluation in anhydrous aerosols.

EXAMPLE 7

Aqueous polymer solutions were prepared at 2% polymer solids and were evaluated for stiffness according to the following protocol. Results are presented in Table 7.

Stiffness Test Protocol

Each of the polymer solutions was tested on three dampened 4.5 inch Brown Virgin Italian hair swatches. The swatches were dipped in the 2% active aqueous solutions. Excess solution was removed by squeezing the wet swatch between thumb and index finger. The swatches were dried in an oven at 110° F. for 45 minutes. The swatches were placed in a constant temperature and humidity chamber at 50% relative humidity and 23° C. and allowed to remain therein overnight. The stiffness of the swatches were measured using appropriate device for measuring stiffness. The results were statistically analyzed and reported at the 95% confidence level.

TABLE 7

Stiffness Evaluations (2% polymer solids, aqueous concentrates)

| Polymer | Stiffness Units | I.V. |
|---|---|---|
| PVAM | 341 | 0.5 |
| PVP K-90 | ~500 | 2.5 |
| PVF | 315 | 0.4–0.5 |

As the data indicates, PVAM is superior to PVF with respect to stiffness and inferior to PVP K-90, most probably due to the high molecular weight of PVP K-90 relative to the molecular weight of the PVAM polymer. One would expect that similar tests performed on PVP K-30 would indicate that PVAM is superior to PVP K-30, based on the subjective stiffness evaluation. Accordingly, it can be said that PVAM polymers provide stiffness which is as good as some PVP resins.

EXAMPLE 8

Each of the gels prepared above were evaluated for high humidity curl retention according to the following protocol. Results are presented in Table 8.

High Humidity Curl Retention Test Protocol

Each of the gels was tested on nine dampened 10-inch swatches of European Brown hair. To each swatch was applied 0.5 g of the respective gel composition. The gel was worked into the swatch, which then was curled end-over-end on a 0.5 inch teflon mandrel. The curl was then carefully removed from the mandrel and secured with two hair clips. The curl was then placed in an oven at a temperature of 120° F. overnight. The dried curl was gently unwound and hung on a graduated, transparent curl retention board contained in a humidity chamber at 90% relative humidity and 70° F. Percent curl retention was measured at 15, 30, 60, 90 and 120 minutes. Curl retention is calculated as below. The mean % retention obtained at each time interval are compared, statistically analyzed and reported at the 95% confidence level.

$$\text{Curl Retention} = \frac{L - L_f}{L - L_o} \times 100$$

L=Length of swatch fully extended
$L_o$=Length of curl before exposure
$L_f$=Length of curl after exposure

TABLE 8

HIGH HUMIDITY (90%) CURL RETENTION
MEAN RETENTION VALUES (%)
3% Polymer Solids; Alcohol-free Gel Systems

| SAMPLE | 15 MIN | 30 MIN | 60 MIN | 90 MIN | 2 HRS |
|---|---|---|---|---|---|
| PVF | 86 | 66.1 | 44.8 | 36.4 | 32.1 |
| PVP | 84.2 | 68.8 | 46.3 | 38.4 | 34.3 |
| PVAM | 86.7 | 64.6 | 41.3 | 32.5 | 29.5 |

The data indicate that PVAM is comparable both to PVP and to PVF with respect to high humidity curl retention.

Additional PVAM samples were prepared as follows:

Precipitation polymerization of NVAc

In a 2-l flask equipped with a condenser were introduced 22.5 g of NVAM, 225 g of diluent, and, over a 5 minute period, 0.9 mmol of initiator. Two slow-adds were added 10 minutes later, the first one consisting of 177.5 g of NVAM and 458.5 g of diluent and the second one consisting of 5.4 mmol of initiator and 63.5 g of diluent. The slow-adds were added over periods of 3 and 6 hours, respectively, while maintaining reflux in the reaction system. The reaction was continued for one more hour before filtration of the mixture. The precipitated polymer was dried in a heated oven to remove the diluent.

In one sample, ethyl acetate was used as the diluent and t-amylperoxy pivalate (t-APP) was used as the initiator. In another sample, acetone was used as the diluent and T-APP as the initiator. In another sample, acetone was used as the diluent and α-cumyl peroxyneodecanoate as the initiator.

In a 2-L flask equipped with a condenser were introduced 22.5 g of NVAM and 225 g of ethyl acetate, and, over a 5 minute period, 0.22 g of t-APP in 25 g of ethyl acetate. A slow-add consisting of 177.5 g of NVAM and 458.5 g of ethyl acetate was added 10 minutes later. It was added over a period of 2.5 hours. A second slow-add was started 1.5 hours after the beginning of the first slow-add. The second slow-add consisted of 1.36 g of t-APP in 63.5 g of ethyl acetate. This addition was conducted over a 4 hour period. Reflux was maintained during the slow-additions. At the end of the second slow-add, the mixture was maintained at reflux for an additional hour. The resulting precipitate was filtered to generate a wet polymer cake.

We claim:

1. A hair care gel composition, consisting essentially of:
   an essentially non-crosslinked polymer in an amount effective to provide the hair care composition with a property selected from the group consisting of a hair fixative property and a hair conditioning property, wherein the polymer is selected from the group consisting of a homopolymer prepared from N-vinyl acetamide monomer and an interpolymer prepared from N-vinyl acetamide monomer and a vinyl monomer;
   a gelling agent in an amount effective to form a gel, wherein said gelling agent is selected from the group consisting of synthetic polymers, cellulosic thickeners, starch based thickeners, and naturally occurring gums; and
   at least one Ingredient selected from the group consisting of a conditioning agent, a rheology modifier, an opacifier, a stabilizer, an emulsifier, a preservative, a sequestering agent, a pearling agent, a clarifying agent, a fragrance, a colorant, a propellant, an organic solvent and water.

2. The hair care gel composition of claim 1 comprising from about 0.05 to about 15 weight percent of the polymer.

3. The hair care gel composition of claim 2 wherein the vinyl monomer is selected from the group consisting of (a) styrene and derivatives thereof, (b) $C_1$–$C_{18}$ alkyl esters of acrylic acid, (c) $C_1$–$C_{18}$ alkyl esters of methacrylic acid, (d) vinyl esters of the formula $CH_2$=CH—OCOR where R is $C_1$–$C_{18}$, (e) alkyl-substituted acrylamides and methacrylamides of the formula $CH_2$=CR—$CONR_1R_2$ where R is H or $CH_3$; $R_1$ is H or $C_1$–$C_{12}$ and $R_2$ is $C_1$–$C_{18}$, (f) monoesters and diesters of fumaric, itaconic and maleic acids, (g) vinyl ethers, (h) hydroxy functional acrylates and methacrylates, (i) vinyl monomers containing an amine selected from the group consisting of secondary, tertiary and quaternary amines, (j) acrylamide, (k) non-alkyl-substituted acrylamides and (l) cyclic amides.

4. The hair care gel composition of claim 1 comprising from about 0.1 to about 10 weight percent of the polymer.

5. The hair care gel composition of claim 2 comprising from about 0.05 to about 3 weight percent of a gelling agent, thereby forming a gel.

6. The hair care gel composition of claim 5 wherein the polymer is prepared with from about 100 to 10 weight percent of the N-vinyl acetamide monomer and from 0 to about 90 weight percent of the vinyl monomer.

7. The hair care gel composition of claim 6 wherein the vinyl monomer is selected from the group consisting of methyl acrylate, methyl methacrylate, 2-hydroxyethyl acrylate, 2-hydroxyethyl methacrylate, 2-hydroxypropyl acrylate, 2-hydroxypropyl methacrylate, vinyl acetate, oligoethylene glycol monomethacrylate, methacrylatoethyltrimethyl ammonium chloride, methacrylatoethyltrimethyl ammonium sulfate and dimethyl diallyl ammonium chloride.

8. A method for treating hair, the method comprising:
   applying to the hair a hair care gel composition, which composition consists essentially of
   an essentially non-crosslinked polymer in an amount effective to provide the hair care composition with a property selected from the group consisting of a hair fixative property and a hair conditioning property, wherein the polymer is selected from the group consisting of a homopolymer prepared from N-vinyl acetamide monomer and an interpolymer prepared from N-vinyl acetamide monomer and a vinyl monomer;
   a gelling agent in an amount effective to form a gel, wherein said gelling agent is selected from the group consisting of synthetic polymers, cellulosic thickeners, starch based thickeners, and naturally occurring gums; and at least one Ingredient selected from the group consisting of a conditioning agent, an emulsifier, a rheology modifier, an opacifier, a stabilizer, a preservative, a sequestering agent, a pearting agent, a clarifying agent, a fragrance, a colorant, a propellant, an organic solvent and water; and optionally, removing excess hair care composition from the hair.

9. The method of claim 8 wherein the hair care gel composition comprises from about 0.05 to about 15 weight percent of the polymer.

10. The method of claim 9 wherein the hair care gel composition comprises from about 0.05 to about 3 weight percent of the gelling agent.

11. The method of claim 10 wherein the vinyl monomer is selected from the group consisting of (a) styrene and derivatives thereof, (b) $C_1$–$C_{18}$ alkyl esters of acrylic acid, (c) $C_1$–$C_{18}$ alkyl esters of methacrylic acid, (d) vinyl esters of the formula $CH_2$=CH—OCOR where R is $C_1$–$C_{18}$, (e) alkyl-substituted acrylamides and methacrylamides of the formula $CH_2$=CR—$CONR_1R_2$ where R is H or $CH_3$; $R_1$ is H or $C_1$–$C_{12}$ and $R_2$ is $C_1$–$C_{18}$, (f) monoesters and diesters of fumaric, itaconic and maleic acids, (g) vinyl ethers, (h) hydroxy functional acrylates and methacrylates, (i) vinyl monomers containing at least one amine group selected from the group consisting of secondary, tertiary and quaternary amines, (j) acrylamide, (k) non-alkyl-substituted acrylamides, and (l) cyclic amides.

12. The method of claim 10 wherein the polymer is prepared in the absence of polymerizable compounds having at least two unsaturated groups in one molecule.

13. A hair care gel composition, consisting essentially of:

an essentially non-crosslinked polymer in an amount effective to provide the hair care composition with a property selected from the group consisting of a hair fixative property and a hair conditioning property, wherein the polymer is selected from the group consisting of a homopolymer prepared from N-vinyl acetamide monomer and an interpolymer prepared from N-vinyl acetamide monomer and a vinyl monomer;

from about 0.1 to about 1.0% of a gelling agent selected from the group consisting of synthetic polymers, cellulosic thickeners, starch based thickeners, and naturally occurring gums; and at least one ingredient selected from the group consisting of a conditioning agent, a rheology modifier, an opacifier, a stabilizer, an emulsifier, a preservative, a sequestering agent, a pearling agent, a clarifying agent, a fragrance, a colorant, a propellant, an organic solvent and water.

14. The hair care gel composition of claim 13 comprising from about 0.05 to about 15 weight percent of the polymer.

15. The hair care gel composition of claim 14 wherein the vinyl monomer is selected from the group consisting of (a) styrene and derivatives thereof, (b) $C_1$–$C_{18}$ alkyl esters of acrylic acid, (c) $C_1$–$C_{18}$ alkyl esters of methacrylic acid, (d) vinyl esters of the formula $CH_2$=CH—OCOR where R is $C_1$–$C_{18}$, (e) alkyl-substituted acrylamides and methacrylamides of the formula $CH_2$=CR—$CONR_1R_2$ where R is H or $CH_3$; $R_1$ is H or $C_1$–$C_{12}$ and $R_2$ is $C_1$–$C_{18}$, (f) monoesters and diesters of fumaric, itaconic and maleic acids, (g) vinyl ethers, (h) hydroxy functional acrylates and methacrylates, (i) vinyl monomers containing an amine selected from the group consisting of secondary, tertiary and quaterna amines, (j) acrylamide, (k) non-alkyl-substituted acrylamides and (l) cyclic amides.

16. The hair care gel composition of claim 13 comprising from about 0.1 to about 10 weight percent of the polymer.

17. The hair care gel composition of claim 13 wherein the polymer is prepared with from about 100 to 10 weight percent of the N-vinyl acetamide monomer and from 0 to about 90 weight percent of the vinyl monomer.

18. The hair care gel composition of claim 17 wherein the vinyl monomer is selected from the group consisting of methyl acrylate, methyl methacrylate, 2-hydroxyethyl acrylate, 2-hydroxyethyl methacrylate, 2-hydroxypropyl acrylate, 2-hydroxypropyl methacrylate, vinyl acetate, oligoethylene glycol monomethacrylate, methacrylatoethyltrimethyl ammonium chloride, methacrylatoethyltrimethyl ammonium sulfate and dimethyl diallyl ammonium chloride.

19. A method for treating hair, the method comprising:

applying to the hair a hair care gel composition, which composition consists essentially of an essentially non-crosslinked polymer in an amount effective to provide the hair care composition with a property selected from the group consisting of a hair fixative property and a hair conditioning property, wherein the polymer is selected from the group consisting of a homopolymer prepared from N-vinyl acetamide monomer and an interpolymer prepared from N-vinyl acetamide monomer and a vinyl monomer;

from about 0.1 to about 1.0% of a gelling agent selected from the group consisting of synthetic polymers, cellulosic thickeners, starch based thickeners, and naturally occurring gums; and at least one ingredient selected from the group consisting of a conditioning agent, an emulsifier, a rheology modifier, an opacifier, a stabilizer, a preservative, a sequestering agent, a pearling agent, a clarifying agent, a fragrance, a colorant, a propellant, an organic solvent and water; and optionally, removing excess hair care composition from the hair.

20. The method of claim 19 wherein the hair care gel composition comprises from about 0.05 to about 15 weight percent of the polymer.

21. The method of claim 20 wherein the hair care gel composition comprises from about 0.05 to about 3 weight percent of the gelling agent.

22. The method of claim 21 wherein the vinyl monomer is selected from the group consisting of (a) styrene and derivatives thereof, (b) $C_1$–$C_{18}$ alkyl esters of acrylic acid, (c) $C_1$–$C_{18}$ alkyl esters of methacrylic acid, (d) vinyl esters of the formula $CH_2$=CH—OCOR where R is $C_1$–$C_{18}$, (e) alkyl-substituted acrylamides and methacrylamides of the formula $CH_2$=CR—$CONR_1R_2$ where R is H or $CH_3$; $R_1$ is H or $C_1$–$C_{12}$ and $R_2$ is $C_1$–$C_{18}$, (f) monoesters and diesters of fumaric, itaconic and maleic acids, (g) vinyl ethers, (h) hydroxy functional acrylates and methacrylates, (i) vinyl monomers containing at least one amine group selected from the group consisting of secondary, tertiary and quaternary amines, (j) acrylamide, (k) non-alkyl-substituted acrylamides, and (l) cyclic amides.

23. The method of claim 21 wherein the polymer is prepared in the absence of polymerizable compounds having at least two unsaturated groups in one molecule.

* * * * *